United States Patent [19]

Pasternak

[11] Patent Number: 5,238,573
[45] Date of Patent: Aug. 24, 1993

[54] SEPARATION OF ORGANIC LIQUIDS

[75] Inventor: Mordechai Pasternak, Spring Valley, N.Y.

[73] Assignee: Texaco Inc., White Plains, N.Y.

[21] Appl. No.: 865,536

[22] Filed: Apr. 9, 1992

[51] Int. Cl.$^5$ .............................................. B01D 61/36
[52] U.S. Cl. ................................. 210/640; 210/654; 210/500.27
[58] Field of Search ................... 210/500.37, 634, 644, 210/649–654, 640, 500.27, 500.41

[56] References Cited

U.S. PATENT DOCUMENTS 4,798,674 1/1989 Pasternak et al. .................. 210/640
4,877,529 10/1989 Pasternak et al. ............... 210/500.37

Primary Examiner—Frank Sever
Attorney, Agent, or Firm—James J. O'Loughlin; Carl G. Seutter

[57] ABSTRACT

Mixtures containing methanol and dimethyl carbonate or methanol and methyl t-butyl ether may be treated by pervaporation to recover product containing decreased quantity of methanol.

12 Claims, No Drawings

SEPARATION OF ORGANIC LIQUIDS

FIELD OF THE INVENTION

This invention relates to the separation of organic liquids. More particularly it relates to removal of methanol from reaction mixtures containing products such as methyl t-butyl ether or dimethyl carbonate.

BACKGROUND OF THE INVENTION

As is well known to those skilled in the art, it is possible to separate mixtures of liquids by various techniques including adsorption or distillation. These conventional processes, particularly distillation, are however characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the charge components form an azeotrope, additional problems may be present which for example, could require that separation be effected in a series of steps (e.g. as in two towers) or by addition of extraneous materials to the system.

There are also comparable problems which are encountered in adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
|---|---|
| Polyyvinyl alcohol containing glycerine | Kuraray Co. Japanese Patent 81/193495 (1981) JP 58/g5522A2 (1983) |
| Nafion brand of perfluorosulfonic acid | Cabasso and Liu J. Memb. Sci. 24, 101 (1985) |
| Sulfonated polyethylene | Cabasso, Korngold, & Liu, J. Pol. Sci.: Letters, 23, 57 (1985) |
| Fluorinated Polyether or Carboxylic Acid Fluorides | U.S. Pat. No. 4,526,948 to DuPont as assignee of Resnickto |
| Selemion AMV blend of Asahi Glass cross-linked styrene - butadiene (with quaternary ammonium residues on a polyvinyl chloride backing | Wentzlaff, Boddeker, & Hattanbach J. Memb. Sci. 22,333 (1985) |
| Cellulose triacetate | Wentzlaff, Boddeker & Hattanback, J. Memb. Sci. 22, 333 (1985) |
| Polyacrylonitrile or Polytetrafluoroethylene grafted with N-vinyl pyrrolidone | Neel, Aptel, & Clement Desalination 53, 297 (1985) |
| Cellulose Acetate and others | Proc. of Int. Mem. Conf. Sept., 1986 Ottawa, p 229 |
| Crosslinked Polyvinyl Alcohol | Eur. Patent 0 096 339 to GFT as assignee of Bruschke |
| Poly(maleimide- acrylonitrile) | Yoshikawa et al J. Pol. Sci. 22, 2159 (1984) |
| Dextrine - isophoronediisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent 0 096 339 A2 of GFT as assignee of Bruschke—published 21 Dec. 1983.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

U.S. Pat. No. 4,952,318, issued Aug. 28, 1990, (and its divisional U.S. Pat. No. 5,006,576 issued Apr. 9, 1991) to M. Pasternak and T. G. Dorawala are directed to separation of dilute aqueous solutions of organic oxygen-containing components by use of, as a pervaporation membrane, an ion exchange resin in membrane form bearing a pendant acid group, which membrane has been contacted with a quaternary ammonium salt.

U.S. Pat. No. 4,798,674, issued Jan. 17, 1989, (and its divisional 4,877,529 issued Oct. 31, 1989) to M. Pasternak, C. R. Bartels, and J. Reale, Jr. is directed to the separation of methanol from products such as methyl t-butyl ether or dimethyl carbonate by use of, as a pervaporation membrane, either (i) a cross-linked polyvinyl alcohol membrane or (ii) an ion exchange membrane which has been contacted with a quaternary ammonium salt.

U.S. Pat. No. 4,960,519 issued Oct. 20, 1990, to M. Pasternak, C. R. Bartels, J. Reale, Jr., and V. Shah is directed to separation of alcohols from oxygenates by use, as a pervaporation membrane, of a blend of a polyvinyl alcohol and a polyacrylic acid on a polyacrylonitrile support layer.

U.S. Pat. No. 4,898,674 issued Feb. 6, 1990 to M. Pasternak and T. G. Dorawala is directed to changing the ratio of components in a mixture of components (typically toluene and methyl ethyl ketone) in a dewaxing solvent by use, as a pervaporation membrane, of an ion exchange polymer in membrane form which has been contacted with tetraphenyl phosphonium bromide or a salt of an alkali metal (such as potassium chloride).

It is an object of this invention to provide a separation process. Other objects will be apparent to those skilled in the art.

STATEMENT OF THE INVENTION

In accordance with certain of its aspects, this invention is directed to a method of concentrating a charge solution containing (i) an alcohol having less than three carbon atoms and (ii) an oxygenate having at least three carbon atoms selected from the group consisting of organic ethers, aldehydes, ketones, and esters which comprises maintaining, as a pervaporation membrane, a high molecular weight, ion-exchange resin in membrane form having carbon atoms in the backbone bearing a pendant acid group, which membrane has been contacted with a solution of a metal salt;

maintaining a pressure drop across said pervaporation membrane;

passing a charge solution containing (i) an alcohol having less than three carbon atoms and (ii) an oxygenate having at least three carbon atoms selected from the group consisting of organic ethers, aldehydes, ketones, and esters into contact with the high pressure side of said pervaporation membrane whereby at least a portion of said alcohol in said charge solution and a lesser portion of oxygenate pass by pervaporation through said pervaporation membrane as a lean mixture containing more alcohol and less oxygenate than are present in said charge solution and said charge solution is converted to a rich liquid containing less alcohol and more oxygenate than are present in said charge solution;

recovering as permeate from the low pressure side of said pervaporation membrane said lean mixture containing more alcohol and less oxygenate than are present in said charge solution, said lean mixture being recovered in vapor phase at a pressure below the vapor pressure thereof; and recovering as retentate from the high pressure side of said pervaporation membrane said rich liquid containing a lower alcohol content and a higher oxygenate content than are present in said charge solution.

DESCRIPTION OF THE INVENTION

The pervaporation membrane which may be employed in practice of this invention is a high molecular weight, ion exchange resin in membrane form bearing pendant acid groups. The membrane may be formed of an ion exchange material such as polyolefin (e.g. polyethylene, polypropylene, polystyrene, copolymers of ethylene-propylene, terpolymers of ethylenepropylene-third monomer such as 1,4-hexadiene or dicyclopentadiene or ethylidenenorbornene); vinyls such as polyvinyl chloride, polyvinyl acetate, etc. The molecular weight of the membrane may vary depending on the species. The thickness of the membrane may typically be 130-430 microns, say 190 microns.

The ion exchange resins which may be employed in membrane form are characterized by the presence of a pendant acid group such as a —COOH group or more preferably a —SO$_3$H group. These pendant groups may be introduced into the resin in known manner, if not already present therein, by functionalization with appropriate reagents.

A preferred class of membranes may include those which are perfluorinated (i.e. contain substantially no hydrogen atoms other than those on the pendant acid e.g. —SO$_3$H groups). These membranes may preferably contain —(CF$_2$CF$_2$)—groups and be characterized by the following formula:

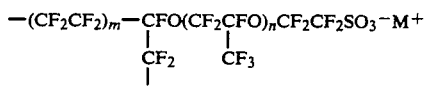

wherein M is hydrogen or a metal such as sodium.

One acid resin membrane which is particularly preferred is that first set forth in the following table which lists illustrative available ion exchange resin membranes which may be employed:

TABLE

A. The Nafion-H 117 brand of perfluorinated resin membrane made by DuPont characterized by a thickness of 190 microns having the structure

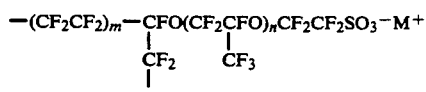

wherein M is hydrogen or a metal such as sodium

B. The Nafion 901 brand of perfluorinated resin membrane (of thickness about 190 microns) which is characterized by the same general formula as A above except that it also contains —COOH groups in addition to —SO$_3$M groups.

C. Sulfonated polyethylene

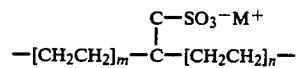

wherein M is hydrogen or a metal such as sodium

TREATMENT OF THE ION EXCHANGE MEMBRANE

Treatment of the ion exchange membranes to render them useful in the process of the instant invention includes contacting the surface with a charge preferably aqueous solution of a metal cation, typically derived from a metal salt.

The metal cation which may be employed may be derived from a salt of a metal of Group I-A (Li, Na, K, Rb, Cs), I-B (Cu, Ag, Au), II-A (Be, Mg, Ca, Sr, Ba), II-B (Zn, Cd, Hg), III-A (Al, Ga, In), III-B (Sc, Y or the rare earths of atomic number 57-71), IV-A (Si, Ge, Sn, Pb), IV-B (Ti, Zr), V-A (As, Sb, Bi), V-B (V, Nb, Ta), VI-A (Se, Te), VI-B (Cr, Mo, W), VII-B (Mn, Re). or VIII non-noble (Fe, Co, Ni) or noble (Ru, Rh, Pd, Os, Ir, Pt).

The preferred salts are salts of metals of Groups I-A, I-B, II-A, or VI-B. Most preferred are the alkali metals of Group I-A and particularly Cs, K, Na, or Li. As hereinafter noted, cesium yields highest Selectivity (albeit at low Flux) while lithium yields highest Flux (albeit at low Selectivity). Sodium generally is found to yield good Selectivity at reasonable Flux.

The anion of the salt may be an anion which yields a salt which is soluble in the solvent to be employed to treat the membrane. Typical anions may include inorganic anions such as halide (typically chloride), sulfate, nitrate, etc. or organic anions such as oxalate, acetate, propionate, sulfonate, phthalate, etc.

It is preferred to utilize sodium chloride or sodium bromide (as the source of the Na$^+$ counterion) in aqueous solution. Non-aqueous media may be employed in which case the salt will be one which is soluble in the selected medium which may be an amine (such as pyridine), an ether (such as ethyl ether), an ester (such as ethyl acetate), a ketone, etc.

Illustrative salts which may be employed may include the following:

TABLE

| Salt | Solvent |
| --- | --- |
| NaCl | Water |
| KCl | " |
| CsCl | " |
| LiCl | " |
| $CaCl_2$ | " |
| $LiNO_3$ | " |
| $BaCl_2$ | " |
| $FeCl_2$ | " |
| $NiSO_4$ | " |
| $CoSO_4$ | " |
| $NaNH_4HPO_4$ | Acetone |
| $K_2SO_4$ | " |
| $Na_2(COO)_2$ | Ethyl ether |
| $KBO_2$ | " |
| $Li_2(COO)_2$ | " |
| $NaBH_4$ | Pyridine |
| $LiNO_3$ | " |
| $NaOOCCH_3$ | Ethanol |
| $NaClO_4$ | " |
| $KOOCC_6H_5$ | " |

In practice of the invention, the acid membrane may be treated with the metal salt in preferably aqueous solution. The salt may be employed as a 5 w %–20 w %, say, 10 w % solution (corresponding to about 1M) in solvent, typically water or an alcohol such as isopropanol. Contact may be at 20° C.–40° C., say 25° C. for 12–48 hours, say 24 hours. Thereafter, the treated membrane may be washed 2–5, say 3 times for 10–50 minutes, say 30 minutes at 20° C.–40° C., say 25° C. with water or isopropanol followed by washes with a 50/50 mixture of isopropanol and water and drying at 20° C.–40° C., say 25° C. for 5–20 minutes, say 10 minutes.

It may be found that treatment of the ion exchange membrane with metal salt gives outstanding results in terms of Separation and Flux.

THE PERVAPORATION MEMBRANE

The membranes of this invention may be utilized in various configurations. In a preferred embodiment, it is possible to utilize the system of this invention as a tubular or hollow fibre membrane.

In operation, the charge liquid may be admitted to the tube side and passes through the inside of the tubes and exits as retentate. During passage through the tubes, permeate passes through the tubular membrane and is collected in the shell side.

PERVAPORATION

It is a feature of the ion exchange pervaporation membrane that it is found to be particularly effective when used in a pervaporation process. In pervaporation, a charge liquid containing a more permeable and a less permeable component is maintained in contact with a pervaporation membrane; and a pressure drop is maintained across that pervaporation membrane. The charge liquid dissolves into the membrane and diffuses therethrough. The permeate which passes through the membrane and exits as a vapor may be recovered by condensing at low temperature or alternatively may be swept away by use of a moving stream of gas. The discharge side of the membrane is maintained at a pressure which is less than the vapor pressure of the permeate. Preferably, the permeate side of the membrane is maintained at a low pressure, typically 5–10 mm. Hg.

For general background on pervaporation, note U.S. Pat. Nos. 4,277,344; 4,039,440; 3,926,798; 3,950,247; 4,035,291; etc.

It is a feature of this invention that the novel membrane may be particularly useful in pervaporation processes for concentrating a charge solution containing (i) an alcohol having less than three carbon atoms and (ii) oxygenate having at least three carbon atoms selected from the group consisting of organic ethers, aldehydes, ketones, and esters.

The oxygenate may be (i) an organic ether such as diethyl ether, di-n-propyl ether, di-n-butyl ether, methyl t-butyl ether, ethyl t-butyl ether, methyl t-amyl ether, ethyl t-amyl ether, etc.; (ii) an aldehyde such as propionaldehyde, butyraldehyde, benzaldehyde, etc.; (iii) a ketone such as acetone, methylethyl ketone, diethyl ketone, etc.; or (iv) an ester such as methyl acetate, methyl propionate, methyl butyrate, methyl benzoate, dimethyl carbonate, diethyl carbonate, etc.

The alcohol may typically be methanol or ethanol. Most favorable results may be obtained with methanol.

It will be obvious to those skilled in the art that the process of this invention may find particular use when the charge mixture to be treated is a reaction product wherein one of the components to be separated is unreacted charge component. A typical such charge mixture is that attained from the reaction of methanol and carbon monoxide wherein the mixture may contain unreacted methanol and product dimethyl carbonate (DMC). Another illustrative charge mixture is that attained from the reaction of methanol and isobutene wherein the reaction mixture may contain methanol and methyl t-butyl ether (MTBE) optionally containing a hydrocarbon such as pentane.

These charge solutions may have been subjected to preliminary separation, e.g. distillation, to yield, for example, an azeotrope of methanol and dimethyl carbonate.

Other charge solutions may include (i) methyl acetate-methanol, (ii) ethyl acetate-ethanol, etc.

It is a particular feature of the process of this invention that it permits attainment of good Selectivity when the charge solution also contains a hydrocarbon diluent-solvent. Hydrocarbon diluent-solvents may typically include those which are present e.g. during the reaction of methanol and isobutylene to form methyl t-butyl ether. These diluent-solvent hydrocarbons may include $C_5$–$C_{10}$ preferably aliphatic hydrocarbons which are liquid at conditions of reaction. A common such hydrocarbon may be pentane.

One such available mixture contains about 7 w % methanol, about 23 w % methyl t-butyl ether, and about 70 w % commercial pentane.

In practice of the pervaporation process of this invention, the charge solution typically at 40° C.–120° C., say 70° C. may be passed into contact with the pervaporation membrane of this invention. A pressure drop of about one atmosphere is commonly maintained across the membrane. Typically, the feed or charge side of the membrane is at about atmospheric pressure and the permeate or discharge side of the membrane is at a pressure of about 0.5–50, preferably 5–20, say 1.5 mm.Hg, or lower.

The permeate which passes through the membrane typically includes e.g. methanol and a small proportion of the oxygenate from the charge liquid. Typically, the permeate contains 90–99 w %, say up to 99+w % methanol. Permeate is recovered in vapor phase.

Pervaporation may typically be carried out at a flux of 0.01–2.5, say about 0.8 kilograms per square meter per hour (kmh). Typically, the units may have a selectivity (measured in terms of w % of e.g. methanol in the permeate during pervaporation at 70° C. of a solution of methanol/MTBE) of 90-99.9 w % methanol. It will vary depending on the oxygenate.

The Separation Factor S which represents the ability of the membrane to recover desired oxygenate is calculated as follows:

$$S = \frac{\left(\frac{X_n}{X_m}\right)_p}{\left(\frac{X_n}{X_m}\right)_f}$$

wherein $X_n$ and $X_m$ are the weight fractions of alcohol component and oxygenate respectively in the permeate (P) and the feed (F). A system showing no separation at all would have a Separation Factor of 1; and a system showing perfect 100% separation would have a Separation Factor of infinity.

Practice of the process of this invention will be apparent to those skilled in the art from inspection of the following examples wherein, as elsewhere in this specification, all parts are parts by weight unless otherwise stated. An asterisk indicates a control example.

EXAMPLE I

In this Example which represents the best mode presently known, the charge solution is a homogeneous liquid at 70° C. containing 53.9 w % methanol and 46.1 w % methyl t-butyl ether (MTBE).

The membrane employed is the commercially available DuPont Nafion-H 117 symmetric film membrane of thickness of 190 microns and charge capacity of 0.88 meq/gram.

The membrane is immersed in a one mole aqueous solution of sodium chloride for 24 hours at 25° C. The membrane is then washed with water and allowed to equilibrate in the charge MeOH/MTBE solution for 24 hours.

The membrane is then used to effect separation of the charge solution by pervaporation at operating temperature of 70° C. The charge solution is admitted to the pervaporation cell at a rate of 0.2 gallons per minute. The inlet pressure on the membrane is atmospheric pressure; the outlet pressure is 0.5-1 mm. Hg.

The permeate is found to contain 99.4 w % methanol. Separation Factor is 141.7 and the Flux is 0.83 kmh.

EXAMPLES II–XVIII

In this series of Examples, the Nafion-H 117 membranes are treated to introduce counterions by use of aqueous solutions of metal bromides or chlorides; and the so-formed membranes are used to separate methanol/methyl t-butyl ether charge. The metal halides include halides (chloride or bromide) of lithium (Li), sodium (Na), potassium (K), and cesium (Cs). The procedure of Example I is generally followed.

TABLE

Performance of Ion Exchange Membranes with Methanol/MTBE Feed

| Example | Membrane | Temperature (°C.) | Feed (% Methanol) | Permeate (% Methanol) | Separation Factor | Flux (kmh) |
|---|---|---|---|---|---|---|
| II | Nafion—Li | 30 | 81.3 | 95.9 | 5.4 | 0.84 |
| III | | 50 | 80.9 | 96.1 | 5.8 | 0.84 |
| IV | | 70 | 64.0 | 96.7 | 16.5 | 1.65 |
| V | Nafion—Na | 30 | 80.3 | 99.4 | 40.6 | 0.41 |
| VI | | 50 | 77.4 | 99.5 | 58.1 | 0.54 |
| I | | 70 | 53.9 | 99.4 | 141.7 | 0.83 |
| VII | Nafion—K | 30 | 82.1 | 99.6 | 54.3 | 0.04 |
| VIII | | 50 | 81.6 | 99.9 | 225.3 | 0.07 |
| IX | | 70 | 71.8 | 99.8 | 196.0 | 0.12 |
| X | Nafion—Cs | 30 | 83.5 | 99.3 | 196.2 | 0.01 |
| XI | | 50 | 80.8 | 99.9 | 237.4 | 0.03 |
| XII | | 70 | 77.9 | 99.9 | 283.4 | 0.08 |
| XIII | Nafion—H 117 | 30 | 81.7 | 99.9 | 223.8 | 0.01 |
| XIV | | 50 | 79.4 | 99.9 | 259.2 | 0.03 |
| XV | | 70 | 72.4 | 99.9 | 380.8 | 0.06 |
| XVI | Nafion—Li | 30 | 13.3 | 89.3 | 54.6 | 0.05 |
| XVII | | 50 | 14.2 | 89.0 | 48.6 | 0.06 |
| XVIII | | 70 | 16.2 | 85.2 | 29.8 | 0.08 |

From the above Table, the following conclusions inter alia may be drawn:

(i) Use of alkali metal counterions permits attainment of outstanding results;

(ii) Use of cesium counterions permits attainment of highest Separation Factor;

(iii) Use of lithium counterions permits attainment of highest Flux;

(iv) Use of sodium counterions permits attainment of best results—judged in terms of a reasonable balance between high Separation Factor and high Flux;

(v) Selectivity (i.e. Separation Factor) generally increases as the atomic weight of the counterion increases (Cs>K>Na>Li);

(vi) Flux generally increases as the atomic weight of the counterion decreases (Li>Na>K>Cs);

(vii) Both Separation Factor and Flux increase as the temperature increases in the 30° C.–70° C. range;

(viii) The process of the instant invention shows improved results when compared to the Nafion-H 117. Although it is possible to attain better Separation with the latter (e.g. 380.8 v 141.7), this is attained at significantly lower Flux (0.06 v 0.83).

(ix) The process is effective over a broad range which includes low concentrations of methanol.

EXAMPLES XIX–XXVI

In this series of examples, the charge contains about 5%–7% methanol. 23%–25% MTBE, and about 70 w % pentane.

TABLE

Performance of Ion-Exchange and Composite Membranes
with 7% Methanol/23% MTBE/70% Pentane Feed

| Example | Membrane | Temperature (°C.) | Feed (% Methanol) | Permeate (% Methanol) | Separation Factor | Flux (kmh) |
|---|---|---|---|---|---|---|
| XIX | Nafion—Li | 30 | 5.4 | 95.1 | 337 | 0.07 |
| XX | | 50 | 5.4 | 95.9 | 412 | 0.04 |
| XXI | Nafion—Na | 30 | 7.3 | 97.1 | 426 | 0.07 |
| XXII | | 50 | 6.0 | 93.3 | 220 | 0.03 |
| XXIII | Nafion—K | 30 | 6.5 | 99.8 | 7977 | 0.006 |
| XXIV | | 50 | 6.5 | 99.95 | 23960 | 0.005 |
| XXV | Nafion—Cs | 30 | 7.3 | 99.3 | 1908 | 0.006 |
| XXVI | | 50 | 4.4 | 98.1 | 1095 | 0.004 |

From the above Table, it is apparent that:
(i) the process is effective over a broad range which includes low concentration of methanol;
(ii) the process is effective when used with three-component mixtures.

EXAMPLES XXVII–XLI

In this series of Examples, the procedure of Example I is duplicated except that the charge solution contains 73 w % methanol and 27 w % dimethyl carbonate.

TABLE

Performance of Ion Exchange Membranes with
73% Methanol/27% DMC Azeotrope

| Example | Membrane | Temperature (°C.) | Permeate (% Methanol) | Separation Factor | Flux (kmh) |
|---|---|---|---|---|---|
| XXVII | Nafion—Li | 30 | 78.5 | 1.3 | 0.92 |
| XXVIII | | 50 | 77.8 | 1.4 | 1.38 |
| XXIX | | 70 | 78.5 | 1.6 | 2.03 |
| XXX | Nafion—Na | 30 | 85.1 | 2.2 | 0.66 |
| XXXI | | 50 | 86.0 | 2.5 | 0.97 |
| XXXII | | 70 | 85.9 | 2.5 | 1.35 |
| XXXIII | Nafion—K | 30 | 88.9 | 3.3 | 0.02 |
| XXXIV | | 50 | 86.5 | 2.6 | 0.05 |
| XXXV | | 70 | 88.5 | 3.3 | 0.13 |
| XXXVI | Nafion—Cs | 30 | 85.1 | 2.2 | 0.09 |
| XXXVII | | 50 | 84.6 | 2.1 | 0.26 |
| XXXVIII | | 70 | 84.6 | 2.2 | 0.36 |
| XXXIX | Nafion—H 117 | 30 | 89.2 | 3.3 | 0.03 |
| XL | | 50 | 86.8 | 2.6 | 0.07 |
| XLI | | 70 | 86.7 | 2.6 | 0.14 |

Results comparable to those of Example I may be attained if the counterion as:

| Example | Counterion |
|---|---|
| XLII | Mg |
| XLIII | Al |
| XLIV | Cu |
| XLV | Cr |
| XLVI | Co |

Results comparable to those of Example I may be attained if the membrane (to which the counterion is bonded) is:

TABLE

| EXAMPLE | MEMBRANE |
|---|---|
| XLVII | Nafion 901 brand of perflorinated resin with carboxylic and sulfonic groups |
| XLVIII | Sulfonated polyethylene |

Although this invention has been illustrated by reference to specific embodiments, it will be apparent to those skilled in the art that various charges and modifications may be made which clearly fall within the scope of the invention.

What is claimed:

1. The method of concentrating a charge solution containing (i) an alcohol having less than three carbon atoms and (ii) an oxygenate having at least three carbon atoms selected from the group consisting of organic ethers, aldehydes, ketones, and esters which comprises
maintaining, as a pervaporation membrane, a high molecular weight ion exchange resin in membrane form having carbon atoms in the backbone bearing a pendant acid group, which membrane has been contacted with a solution of a metal salt;
maintaining a pressure drop across said pervaporation membrane;
passing a charge solution containing (i) an alcohol having less than three carbon atoms and (ii) an oxygenate selected from the group consisting of organic ethers, aldehydes, ketones, and esters into contact with the high pressure side of said pervaporation membrane whereby at least a portion of said alcohol in said charge solution and a lesser portion of oxygenate pass by pervaporation through said pervaporation membrane as a lean mixture containing more alcohol and less oxygenate than are present in said charge solution and said charge solution is converted to a rich liquid containing less alcohol and more oxygenate than are present in said charge solution, said method enabling attainment of a balance between separation factor and flux;
recovering as permeate from the low pressure side of said pervaporation membrane said lean mixture containing more alcohol and less oxygenate than are present in said charge solution, said lean mixture being recovered in vapor phase at a pressure below the vapor pressure thereof; and recovering as retentate from the high pressure side of said pervaporation membrane said rich liquid containing a lower alcohol content and a higher oxygenate content than are present in said charge solution.

2. The method claimed in claim 1 wherein said metal salt is a salt of a metal of Group I-A, I-B, II-A or VI-B.

3. The method claimed in claim 1 wherein said metal salt is a salt of a metal of Group I-A.

4. The method claimed in claim 1 wherein said metal salt is a salt of sodium.

5. The method claimed in claim 1 wherein said metal salt is sodium chloride.

6. The method claimed in claim 1 wherein said contacting has been effected with an aqueous solution of sodium chloride.

7. The method claimed in claim 1 wherein said alcohol is methanol.

8. The method claimed in claim 1 wherein said charge solution contains methanol and dimethyl carbonate.

9. The method claimed in claim 1 wherein said charge solution contains methanol and methyl t-butyl ether.

10. The method claimed in claim 1 wherein said pervaporation membrane is a high molecular weight ion exchange resin in membrane form having carbon atoms in the backbone bearing a pendant acid group, which resin is characterized by the formula:

$$-(CF_2CF_2)_m-\underset{\underset{|}{CF_2}}{CFO}(CF_2\underset{|}{\overset{|}{CFO}})_n CF_2CF_2SO_3^-M^+$$
$$\phantom{-(CF_2CF_2)_m-CFO(CF_2}CF_3$$

wherein M is a metal said membrane having been contacted with an aqueous solution sodium chloride.

11. The method of concentrating a charge solution containing methanol and methyl t-butyl ether which comprises maintaining, as pervaporation membrane, a high molecular weight ion exchange resin bearing a pendant acid group, which resin is characterized by the formula:

$$-(CF_2CF_2)_m-\underset{\underset{|}{CF_2}}{CFO}(CF_2\underset{|}{\overset{|}{CFO}})_n CF_2CF_2SO_3^-M^+$$
$$\phantom{-(CF_2CF_2)_m-CFO(CF_2}CF_3$$

wherein M is a metal, said membrane having been contacted with an aqueous solution sodium chloride;

maintaining a pressure drop across said pervaporation membrane;

passing a charge solution containing methanol and methyl t-butyl into contact with the high pressure side of said pervaporation membrane whereby at least a portion of said methanol in said charge solution and an lesser portion of said methyl t-butyl ether pass by pervaporation through said pervaporation membrane as a lean mixture containing more methanol and less methyl t-butyl ether than are present in said charge solution and said charge solution is converted to a rich mixture containing less methanol and more methyl t-butyl ether than are present in said charge solution;

recovering as permeate from the low pressure side of said pervaporation membrane said lean mixture containing a lower methanol content and a higher methyl t-butyl ether content than are present in said charge solution;

recovering as retentate from the high pressure side of said pervaporation membrane said rich mixture containing less methanol and more methyl t-butyl ether than are present in said charge solution, said method enabling attainment of a balance between separation factor and flux.

12. The method of concentrating a charge solution containing methanol and methyl t-butyl ether as claimed in claim 11 wherein said charge solution also contains a liquid $C_5$–$C_{10}$ hydrocarbon.

* * * * *